(12) United States Patent
He et al.

(10) Patent No.: US 7,691,590 B2
(45) Date of Patent: Apr. 6, 2010

(54) REDUCING MYELIN-MEDIATED INHIBITION OF AXON REGENERATION

(75) Inventors: Zhigang He, Boston, MA (US); Kevin C. Wang, Boston, MA (US); Vuk Koprivica, Boston, MA (US); Jieun A. Kim, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 75 days.

(21) Appl. No.: 11/958,632

(22) Filed: Dec. 18, 2007

(65) Prior Publication Data

US 2008/0188411 A1    Aug. 7, 2008

Related U.S. Application Data

(63) Continuation of application No. 10/127,058, filed on Apr. 19, 2002, now Pat. No. 7,309,485, which is a continuation of application No. 10/006,002, filed on Dec. 3, 2001, now abandoned.

(51) Int. Cl.
*G01N 33/53* (2006.01)
*G01N 33/68* (2006.01)
*G01N 33/58* (2006.01)
*G01N 33/577* (2006.01)

(52) U.S. Cl. .................. 435/7.2; 435/7.1; 435/7.21; 435/7.92; 435/40.5; 435/69.1; 436/501

(58) Field of Classification Search .................. None
See application file for complete search history.

(56) References Cited

U.S. PATENT DOCUMENTS 7,119,165 B2 * 10/2006 Strittmatter ............ 530/350
2004/0259092 A1 * 12/2004 Barske et al. ............ 435/6

* cited by examiner

*Primary Examiner*—Elizabeth C. Kemmerer
*Assistant Examiner*—Kimberly A. Ballard
(74) *Attorney, Agent, or Firm*—Richard Aron Osman

(57) ABSTRACT

Oligodendrocyte-myelin glycoprotein (OMgp)-specific binding agents are used to reduce OMgp-mediated axon growth inhibition. Mixtures of axons and OMgp and mixtures of Nogo receptor (NgR) and OMgp are used in pharmaceutical screens to characterize agents as inhibiting binding of NgR to OMgp and promoting axon regeneration.

9 Claims, No Drawings

REDUCING MYELIN-MEDIATED INHIBITION OF AXON REGENERATION

This application is a continuation of U.S. Ser. No. 10/127,058 (now U.S. Pat. No. 7,309,485), filed Apr. 19, 2002, which is a continuing application of U.S. Ser. No. 10/006,002 filed on Dec. 3, 2001 now abandoned.

This work was supported by Federal Grant No. 1R21NS41999-01 from NINDS. The government may have rights in any patent issuing on this application.

INTRODUCTION

1. Field of the Invention

The invention is in the field of reducing meylin-mediated inhibition of axon regeneration.

2. Background of the Invention

The inhibitory activity associated with myelin is a major obstacle for successful axon regeneration in the adult mammalian central nervous system (CNS)[1,2]. In addition to myelin associated glycoprotein (MAG)[3-4] and Nogo-A[5-7], evidence suggests the existence of other inhibitors in CNS myelin[8]. We show that a glycosylphosphatidylinositol (GPI)-anchored CNS myelin protein, oligodendrocyte-myelin glycoprotein (OMgp), is a potent inhibitor of neurite outgrowth. Like Nogo-A, OMgp contributes significantly to the inhibitory activity associated with CNS myelin. To elucidate the mechanisms that mediate this inhibitory activity of OMgp, we screened an expression library and identified the Nogo receptor (NgR)[9] as a high affinity OMgp binding protein. Cleavage of NgR and other GPI-linked proteins from the cell surface renders dorsal root ganglion axons insensitive to OMgp. Introduction of exogenous NgR confers OMgp-responsiveness to otherwise insensitive neurons. We conclude that OMgp is an physiological neurite outgrowth inhibitor that acts through and is a physiological ligand of the NgR and its associated receptor complex. We show that Interfering with the OMgp/NgR pathway allows lesioned axons to regenerate after injury in vivo.

SUMMARY OF THE INVENTION

The invention provides methods and compositions for reducing OMgp-mediated axon growth inhibition. In one embodiment, the method comprising steps (a) contacting a mixture comprising an axon and isolated OMgp with an agent and under conditions wherein but for the presence of the agent, the axon is subject to growth inhibition mediated by the OMgp; and (b) detecting resultant reduced axon growth inhibition. In an alternative embodiment, the method comprises steps: (a) contacting a mixture comprising an axon and OMgp with an exogenous OMgp-specific binding agent and under conditions wherein but for the presence of the agent, the axon is subject to growth inhibition mediated by the OMgp, whereby the agent binds the OMgp and reduces the growth inhibition; and (b) detecting resultant reduced axon growth inhibition.

These methods may be practiced with isolated neurons in vitro, or with neurons in situ. Suitable agents include (i) a candidate agent not previously characterized to bind OMgp nor reduce axon growth inhibition mediated by OMgp; (ii) a candidate agent not previously characterized to reduce axon growth inhibition mediated by OMgp; (iii) an OMgp-specific antibody fragment; (iv) a soluble NgR peptide sufficient to specifically bind the OMgp and competitively inhibit binding of the OMgp to NgR; etc. In more particular embodiments, the recited isolated OMgp consists essentially of OMgp, particularly wherein the OMgp is soluble and GPI-cleaved and/or the OMgp is recombinantly expressed on a surface of a cell.

The invention also provides methods and compositions for characterizing an agent as inhibiting binding of NgR to OMgp. In one embodiment, this method comprising the steps (a) incubating a mixture comprising NgR, OMgp and an agent under conditions whereby but for the presence of the agent, the NgR and OMgp exhibit a control binding; and (b) detecting a reduced binding of the NgR to the OMgp, indicating that the agent inhibits binding of the NgR to the OMgp.

The method may be practiced in a variety of alternative embodiments, such as (i) wherein at least one of the NgR and OMgp is soluble and GPI-cleaved; (ii) wherein one of the NgR and OMgp is soluble and GPI-cleaved and the other is membrane-bound; (iii) wherein at least one of the NgR and OMgp is recombinantly expressed on a surface of a cell; etc.

The invention also provides compositions and mixtures specifically tailored for practicing the subject methods. For example, an in vitro mixture for use in the subject binding assays comprises NgR, OMgp and an agent, wherein at least one of the NgR and OMgp is soluble and GPI-cleaved. Kits for practicing the disclosed methods may also comprise printed or electronic instructions describing the applicable subject method.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

In one embodiment, the invention provides a method for reducing axon growth inhibition mediated by OMgp and detecting resultant reduced axon growth inhibition, the method comprising steps: contacting a mixture comprising an axon and isolated OMgp with an agent and under conditions wherein but for the presence of the agent, the axon is subject to growth inhibition mediated by the OMgp; and detecting resultant reduced axon growth inhibition, indicating that the agent reduces axon growth inhibition mediated by OMgp.

The recited axons are mammalian neuron axons, preferably adult neural axons, which may be peripheral or, preferably CNS neuron axons. As exemplified below, the method may be applied to neural axons in vitro or in situ.

OMgp is a natural, mammalian CNS myelin glycoprotein (see, Habib et al. 1998a, 1998b) which functions as a ligand of the Nogo Receptor (NgR) on CNS axons. OMgp cDNA has been cloned from several species, including human (Genbank Accn No. NM_002544), mouse (Genbank Accn No. NM_019409), and cow (Genbank Accn No. S45673). Note that OMgp cDNA encodes two alternative initiating methionine residues; compare, Genbank Accession Nos. M63623 (human) and S67043 (mouse). OMgp may be membrane-bound through a GPI linkage or cleaved therefrom. As exemplified herein, OMgp may be obtained on or cleaved from naturally expressing myelin. Also as exemplified herein, OMgp may also be expressed recombinantly in suitable recombinant expression systems, wherein functional expression may be confirmed by the growth cone collapsing assays described herein.

The recited isolated OMgp is provided isolated from other components of OMgp's natural myelin mileau, which may be effected by purification from such components or expression of the OMgp in a non-natural system. In particular embodiments, the isolated OMgp is accompanied by other components which provide or interfere with or alter the axon growth inhibitory or NgR binding activity of the OMgp. Preferred isolated OMgp is purified or recombinantly expressed, particularly on a surface of a cell.

The recited agent may be characterized as an OMgp-specific binding agent or, particularly as applied to pharmaceutical screens, an agent not previously characterized to bind OMgp nor reduce axon growth inhibition mediated by OMgp, wherein the agent is a candidate agent and the detecting step characterizes the candidate agent as reducing axon growth inhibition mediated by OMgp. Similarly, the agent may be a candidate agent not previously characterized to reduce axon growth inhibition mediated by OMgp, wherein the detecting step characterizes the candidate agent as reducing axon growth inhibition mediated by OMgp.

Detailed protocols for implementing the recited steps are exemplified below and/or otherwise known in the art as guided by the present disclosure. The recited contacting and detecting steps are tailored to the selected system. In vitro systems provide ready access to the recited mixture using routine laboratory methods, whereas in vivo systems, such as intact organisms or regions thereof, typically require surgical or pharmacological methods. More detailed such protocols are described below. Similarly, the detecting step is effected by evaluating different metrics, depending on the selected system. For in vitro binding assays, these include conventional solid-phase labeled protein binding assays, such as ELISA-type formats, solution-phase binding assays, such as fluorescent polarization or NMR-based assays, etc. For cell-based or in situ assays, metrics typically involve assays of axon growth as evaluated by linear measure, density, host mobility or other function improvement, etc.

In another embodiment, the invention provides a method for reducing axon growth inhibition mediated by OMgp and detecting resultant reduced axon growth inhibition by (a) contacting a mixture comprising an axon and OMgp with an exogenous OMgp-specific binding agent and under conditions wherein the agent binds the OMgp and but for the presence of the agent, the axon is subject to growth inhibition mediated by the OMgp, and (b) detecting resultant reduced axon growth inhibition.

This protocol may similarly be practiced with in vitro or in vivo, particularly in situ, mixtures. Note that in this embodiment, the agent is necessarily an exogenous OMgp-specific binding agent and the recited OMgp need not be isolated, i.e. it may be present in the context of its native myelin. Accordingly, this aspect of the invention provides methods for reducing axon growth inhibition mediated by OMgp in its native mileau. By reducing axon growth inhibition, the methods assist the repair of axons following injury or trauma, such as spinal cord injury. In addition, the methods may be applied to alleviate dysfunction of the nervous system due to hypertrophy of neurons or their axonal projections, such as occurs in diabetic neuropathy.

An OMgp-specific binding agent exogenous to an axon or mixture comprising an axon is not naturally present with the axon or mixture. The OMgp-specific binding agents specifically bind the OMgp of the recited mixture and thereby functionally inhibit the axon collapse and/or NgR binding mediated by the OMgp. Of course, as OMgp-specific, the subject agents inherently do not cross-react with (specifically bind to) structurally distinct NgR ligands, such as NogoA. We have exemplified suitable OMgp binding agents from diverse structures. Initial agents were identified by selecting high affinity OMgp binders from natural NgR peptides. These assays identified a number of OMgp-specific NgR peptides encompassing NgR LRR (leucine rich repeat) sequences, including the exemplified species: hNR260/308, mNR260/308 and rNR260/308. Natural OMgp-specific NgR peptide sequences were subject to directed combinatorial mutation and binding analysis. Resultant synthetic-sequence OMgp-specific peptides include the exemplified species: s1NGR260/308, s2NR260/308 and s3NR260/308. We also used a variety of OMgp peptide immunogens to generate OMgp-specific antibodies and antibody fragments, including the exemplified monoclonal antibodies OM-H2276 and OM-H5831 and the exemplified fragments OMF-H7712 and OMF-H6290. OMgp-specific binding agents are also found in compound libraries, including the exemplified commercial fungal extract and a synthetic combinatorial organo-pharmacophore-biased libraries. Structural characterization of the exemplified OMgp binding agents (XR-178892, XR-397344, XR-573632, SY-73273M, SY-32340L and SY-95734E) is effected by conventional organic analysis.

Of particular interest are size-minimized NgR LRR peptides which effectively compete for OMgp ligand binding. We synthesized and screened large libraries of NgR peptides for their ability to bind OMgp and thereby reduce OMgp-mediated axon growth inhibition. This work identified numerous competitive binding peptides of varying length within a 49 amino acid region of a NgR C-terminal leucine rich repeat, exemplified with human, mouse and rat repeat sequences (hNR260/308, SEQ ID NO: 1; mNR260/308, SEQ ID NO:2; and rNR260/308, SEQ ID NO:3). Competitive peptides demonstrating >20% competitive activity compared with the source 49 mer are subject to combinatorial mutagenesis to generate synthetic peptide libraries from which we screen for even higher affinity binders. Preferred competitive peptides consist, or consist essentially of a size-minimized sequence within the disclosed human source 49mer, preferably a sequence of fewer than 48, 38, 28 or 18 residues, wherein at least 6, 8, 12 or 16 residues are usually required for specific binding. Obtaining additional such native sequence and synthetic competitive peptides involves only routine peptide synthesis and screening in the disclosed binding and growth assays.

In particular applications, the target cells are injured mammalian neurons in situ, e.g. Schulz M K, et al., Exp Neurol. 1998 February; 149(2): 390-397; Guest J D, et al., J Neurosci Res. 1997 Dec. 1; 50(5): 888-905; Schwab M E, et al., Spinal Cord. 1997 July; 35(7): 469-473; Tatagiba M, et al., Neurosurg 1997 March; 40(3): 541-546; and Examples, below. For these in situ applications, compositions comprising the OMgp binding agent may be administered by any effective route compatible with therapeutic activity of the compositions and patient tolerance. For example, for CNS administration, a variety of techniques is available for promoting transfer of therapeutic agents across the blood brain barrier including disruption by surgery or injection, drugs which transiently open adhesion contact between CNS vasculature endothelial cells, and compounds which facilitate translocation through such cells. The compositions may also be amenable to direct injection or infusion, intraocular administration, or within/on implants e.g. fibers such as collagen fibers, in osmotic pumps, grafts comprising appropriately transformed cells, etc.

In a particular embodiment, the binding agent is delivered locally and its distribution is restricted. For example, a particular method of administration involves coating, embedding or derivatizing fibers, such as collagen fibers, protein polymers, etc. with therapeutic agents, see also Otto et al.

(1989) J Neurosci Res. 22, 83-91 and Otto and Unsicker (1990) J Neurosc 10, 1912-1921. The amount of binding agent administered depends on the agent, formulation, route of administration, etc. and is generally empirically determined and variations will necessarily occur depending on the target, the host, and the route of administration, etc.

The compositions may be advantageously used in conjunction with other neurogenic agents, neurotrophic factors, growth factors, anti-inflammatories, antibiotics etc.; and mixtures thereof, see e.g. *Goodman & Gilman's The Pharmacological Basis of Therapeutics, 9th Ed.*, 1996, McGraw-Hill. Exemplary such other therapeutic agents include neuroactive agents such as in Table 1.

TABLE 1

Neuroactive agents which may be used in conjunction with OMgp binding agents.

| | | |
|---|---|---|
| NGF | Heregulin | Laminin |
| NT3 | IL-3 | Vitronectin |
| BDNF | IL-6 | Thrombospondin |
| NT4/5 | IL-7 | Merosin |
| CNTF | Neuregulin | Tenascin |
| GDNF | EGF | Fibronectin |
| HGF | TGFa | F-spondin |
| bFGF | TGFb1 | Netrin-1 |
| LIF | TGFb2 | Netrin-2 |
| IGF-I | PDGF BB | Semaphorin-III |
| IGH-II | PDGF AA | L1-Fc |
| Neurturin | BMP2 | NCAM-Fc |
| Percephin | BMP7/OP1 | KAL-1 |

Abbreviations: NGF, nerve growth factor; NT, neurotrophin; BDNF, brain-derived neurotrophic factor; CNTF, ciliary neurotrophic factor; GDNF, glial-derived neurotrophic factor; HGF, hepatocyte growth factor; FGF, fibroblast growth factor; LIF, leukemia inhibitory factor; IGF, insulin-like growth factor; IL, interleukin; EGF, epidermal growth factor; TGF, transforming growth factor; PDGF, platelet-derived growth factor; BMP, bone morphogenic protein; NCAM, neural cell adhesion molecule.

In particular embodiments, the OMgp binding agent is administered in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. As such the compositions, in pharmaceutically acceptable dosage units or in bulk, may be incorporated into a wide variety of containers, which may be appropriately labeled with a disclosed use application. Dosage units may be included in a variety of containers including capsules, pills, etc.

The invention also provides pharmaceutical screens for inhibitors of Omgp-NgR binding, particularly, methods for characterizing an agent as inhibiting binding of NgR to OMgp by: (a) incubating a mixture comprising NgR, OMgp and an agent under conditions whereby but for the presence of the agent, the NgR and OMgp exhibit a control binding; and (b) detecting a reduced binding of the NgR to the OMgp, indicating that the agent inhibits binding of the NgR to the OMgp.

NgR is a natural, mammalian neural axon protein (Fournier et al., 2001, Nature 409, 341-46) which functions as a receptor for Nogo66 and for OMgp. NgR cDNA has been cloned from several species, including human (Genbank Accn No. BC011787), mouse (Genbank Accn No. NM-022982), and rat (Genbank Accn No. AY028438). NgR may be membrane-bound through a GPI linkage or cleaved therefrom. As exemplified herein, NgR may be obtained on or cleaved from naturally expressing myelin. Also as exemplified herein, NgR may also be expressed recombinantly in suitable recombinant expression systems, wherein functional expression may be confirmed by the growth cone collapsing assays described herein.

The screening method is amenable to a wide variety of different protocols. For example, in particular embodiments, at least one of the NgR and OMgp is soluble and GPI-cleaved, one of the NgR and OMgp is soluble and GPI-cleaved and the other is membrane-bound, and at least one of the NgR and OMgp is recombinantly expressed on a surface of a cell.

The invention also provides compositions and mixtures specifically tailored for practicing the subject methods. For example, an in vitro mixture for use in the subject binding assays comprises premeasured, discrete and contained amounts of NgR, OMgp and an agent, wherein at least one of the NgR and OMgp is soluble and GPI-cleaved. Kits for practicing the disclosed methods may also comprises printed or electronic instructions describing the applicable subject method.

EXAMPLES

OMgp is a Physiological Nogo Receptor Ligand and Inhibitor of Neurite Outgrowth. To examine whether any GPI-linked proteins in CNS myelin may act as inhibitors of neurite outgrowth, we treated purified bovine white matter myelin with phosphatidylinositol-specific phospholipase C (PI-PLC) and examined the released proteins for their ability to alter growth cone morphology in a growth cone collapse assay using embryonic day 13 chick dorsal root ganglia (E13 DRG)[6,9,10]. We found that PI-PLC-released CNS myelin proteins, when added to the DRG culture medium, exhibited potent growth cone collapsing activity. To further characterize the inhibitory activity in the PI-PLC-released proteins, we analyzed solubilized proteins by SDS-PAGE and silver staining and found that a band of approximately 110 kDa in size was significantly enriched in this fraction. Since the size of this band was similar to that of a previously identified CNS myelin protein OMgp[11,12], we used antibodies specific for OMgp to detect enrichment of cleaved OMgp in the PI-PLC supernatants by Western blot. Anti-OMgp antibodies detected a band of comparable size in the PI-PLC-treated supernatants, indicating that OMgp is a component released from CNS myelin by PI-PLC. Next, we examined whether purified recombinant OMgp protein was able to act as an inhibitor of neurite outgrowth in two well-established in vitro assays, the growth cone collapse[6,9,13] and the neurite outgrowth assays[3-7,9]. Similar to the PI-PLC-treated myelin supernatants, purified recombinant polyhistidine-tagged OMgp protein (OM-his), but not proteins purified from control vector-transfected COS-7 cells, induced the collapse of growth cones derived from E13 chick DRG neurons in a dose-dependent manner. The effective concentration for half-maximal response ($EC_{50}$) for OM-his was approximately 1.5 nM. Consistent with it being an inhibitor of neurite outgrowth, the GPI-anchored OMgp protein was found to be highly expressed by myelin basic protein (MBP)-positive mature oligodendrocytes and enriched in the axon-adjacent myelin layers[11,12]. Moreover, OM-his, when presented either as an immobilized substrate or in a soluble form, inhibited neurite outgrowth of cerebellar granule neurons (CGN) from postnatal day 7-9 (P7-9) rats, also in a dose-dependent manner. The OMgp-induced inhibitory responses were similar to that brought about by treatment of the same neurons with an alkaline phosphatase (AP) fusion protein containing the 66 amino acid extracellular domain of Nogo-A (AP-66)[6,9], indicating that OMgp, like Nogo-66, is a potent neurite outgrowth inhibitor.

To further examine the functional importance of OMgp as a CNS myelin associated inhibitor, we used peanut agglutinin (PNA)-Agarose beads[11] to specifically deplete OMgp, but not Nogo-A or MAG, from β-octylglucoside-solublized CNS myelin. We found that while the inhibitory activity in the PNA-depleted myelin was significantly reduced compared to control myelin, the OMgp-enriched eluates from the same PNA column displayed a potent inhibitory activity. We next compared the relative contributions of OMgp with two other known inhibitors, MAG and Nogo-A, to the inhibitory activity associated with CNS Myelin. Anion exchange chromatography was able to biochemically separate MAG and Nogo-A[3,15], but failed to separate OMgp from Nogo-A. Thus, we applied the OMgp-depleted PNA column flow-through myelin fractions onto a Q-Sepharose column and generated fractions enriched in MAG or Nogo-A by sequential elution of the column with increasing concentrations of NaCl. Our data revealed that the fractions enriched in MAG or Nogo-A, similar to the OMgp-enriched eluates from the PNA column, all significantly inhibited neurite outgrowth. Comparisons of the $EC_{50}$ for each of these fractions allowed us to estimate that the OMgp-enriched fraction inhibited neurite outgrowth to a similar extent as the Nogo-A-enriched fraction, but much stronger than the MAG-enriched-fraction. Our result is consistent with previous observations that the major inhibitory activity of CNS myelin resides in the 0.30 to 0.5 M NaCl elution fractions of Sepharose Q columns[15,16], as the majority of OMgp co-fractionates with Nogo-A in this chromatography procedure.

To investigate the mechanisms by which OMgp inhibits neurite outgrowth, we used an expression cloning strategy[9,13,16] to identify cell surface OMgp-binding proteins. An AP fusion protein containing OMgp (AP-OM) was able to bind to the surface of rat P9 CGNs and to induce collapse of E13 chicken DRG growth cones, and thus was used in the cell surface binding assays. From pools of an adult human brain cDNA expression library, we isolated two cDNAs that encoded OMgp-binding proteins. Sequence analysis revealed that both cDNAs contained the full-length coding region of the Nogo-66 receptor (NgR), which had been previously identified as a high-affinity receptor for the extracellular domain of Nogo-A[9]. We then established a CHO cell line stably expressing the NgR and determined the binding affinity of expressed NgR for AP-OM as 5 nM, similar to what had been determined for Nogo-66 (7 nM, ref. 9). These data indicate that NgR is a high-affinity OMgp-binding protein. We next performed co-precipitation experiments by incubating GST or a GST fusion protein containing the entire extracellular domain of NgR (GST-NgR) with OM-his alone or in the presence of AP or AP-66 protein. We found that GST-NgR, but not the control GST protein, bound to OM-his, indicating a direct interaction between NgR and OMgp. We next determined which domain(s) of OMgp was responsible for binding to NgR. Like NgR, OMgp is also a GPI-linked protein containing a leucine-rich repeat (LRR) domain. An AP fusion protein containing only the LRR domain of OMgp (AP-LRR) was found to be sufficient to bind strongly to NgR-expressing cells. In addition, the C-terminal domain with serine-threonine repeats (AP-S/T) alone was also able to bind, though less strongly, to NgR expressing cells.

To further determine how NgR interacted at the molecular level with these two inhibitors, we made a series of deletion constructs of NgR and found that both the LRR and the C-terminal LRR (LRRCT) domains of NgR were required for highest binding to OMgp and that OMgp and Nogo-66 appear to bind overlapping regions of NgR. Consistently, in both cell surface binding and the co-precipitation assay, AP-66 and OM-his proteins competed for binding to NgR. To examine the functional consequences of the molecular interaction of the two ligands with NgR, we compared the collapsing activity of OM-his plus AP-66 with that of OM-his or AP-66 alone. The estimated $EC_{50}$ for OM-his plus Nogo-66 (2.5 nM) was similar to that of OM-his (1.5 nM) and AP-66 (2.3 nM), indicating an additive effect between OM-his and AP-66 in inducing growth cone collapse. As the binding affinities of both OMgp and Nogo-66 to NgR are similar, our results together imply that these two myelin components act independently through NgR to inhibit neurite outgrowth.

As the GPI-linked NgR protein can be released by PI-PLC, we next examined whether PI-PLC treatment could affect axonal responsiveness to OMgp. Consistent with a previous study[9], PI-PLC treatment did not alter the growth cone morphology of E13 chick DRG neurons, but rendered these axons insensitive to Nogo-66. Similarly, PI-PLC treatment also abolished the growth cone-collapsing activity of OMgp. As a control, the growth cone collapsing activity of Semaphorin 3A (Sema 3A)[10,13], known to be mediated by transmembrane receptor molecules including neuropilin-1 and members of the plexin family[18], was not affected by PI-PLC treatment. Even though PI-PLC also cleaves other GPI-anchored proteins on the axonal surface, these results indicated that GPI-anchored proteins, such as NgR, act as necessary signal transducers of the inhibitory activity of OMgp.

To assess whether NgR is capable of mediating OMgp-induced inhibitory activity on neurite outgrowth, we next took a gain-of-function approach to examine whether expression of NgR was able to confer OMgp-responsiveness to otherwise insensitive neurons. It has been shown previously that chick E7 retinal ganglion neurons (RGN) are insensitive to Nogo-66, but that introduction of exogenous NgR in these neurons rendered their growth cones to be responsive to Nogo-66[9]. Using the same strategy, we made a recombinant herpes simplex virus (HSV) that drives expression of a FLAG-tagged full-length human NgR (FLAG-NgR) in infected neurons. Upon infection, 80% of the E7 RGNs expressed the FLAG-NgR protein as assessed by immunocytochemistry with an anti-FLAG antibody. No significant morphological changes were observed in the HSV-infected neurons. Consistent with a previous study[9], expression of FLAG-NgR conferred a growth cone collapse response to Nogo-66 in E7 RGNs. Furthermore, the growth cones of NgR-expressing axons also become collapsible by OMgp. In contrast, a control virus driving the expression of β-galactosidase did not alter the axonal responses of the same neurons to either Nogo-66 or OMgp. Taken together, our results indicate that, like Nogo-66, OMgp acts through NgR and its associated receptor complex to inhibit axon outgrowth. As opposed to Nogo-A, the majority of which is localized intracellularly[5-7], OMgp is predominantly localized on the surfaces of oligodendrocytes and axon-adjacent myelin layers[11,12,14], indicating that OMgp is a physiological ligand of NgR.

Purification, PI-PLC Treatment, and OMgp Depletion of Myelin. Myelin was prepared from white matter of bovine brain according to established protocols[19]. In brief, white matter tissues were homogenized in 0.32 M sucrose in phosphate-buffered saline (PBS) and the crude myelin that banded at the interphase of a discontinuous sucrose gradient (0.32

M/0.85 M) was collected and purified by two rounds of osmotic shock with distilled water and re-isolation over the sucrose gradient. For PI-PLC treatment, aliquots of myelin suspensions in water (10 mg/ml) were incubated with or without 2.5 U/ml PI-PLC (Sigma) at 37° C. for 2 hr, prior to centrifugation (360,000 g for 60 min). The supernatants were concentrated, partitioned in Triton X-114, and used for assays and for detection with Western analysis.

To deplete OMgp, myelin was first solublized with 1% octylglucoside and the resultant extract was passed twice through columns with PNA-Agarose (Vector Laboratories) or control Agarose beads as described previously[12]. The OMgp-enriched fraction was obtained by eluting the PNA-Agarose column with buffer containing 0.5 M D-galactose. As a significant portion of OMgp co-fractionated with Nogo-A in anion exchange columns[12], we enriched MAG or Nogo-A from myelin by applying the flow-through fractions from the PNA-Agarose columns onto a Q-Sepharose (Sigma) column[15]. The column was then eluted stepwise with equal amount of buffers containing 0.15 M (MAG-enriched), 0.45 M (Nogo-A enriched), or 1.0 M NaCl[15]. Aliquots of individual fractions were tested for their inhibitory activity in the neurite outgrowth assay as described previously[15,16,21].

Expression Cloning and Binding Experiments. Sequences encoding mouse OMgp were amplified from Marathon-ready mouse cDNA (Clontech) and confirmed by sequencing analysis, prior to subcloning into the expression vector AP-5[9] for expressing an AP-OM fusion protein tagged with both a polyhistidine and a myc epitope. The resultant plasmid DNA was transfected into COS-7 cells and the secreted protein purified using nickel-Agarose resins (Qiagen).

Cell surface binding and expression cloning were performed as described previously[4,13,17]. To detect AP-OM binding, cultures were washed with binding buffer (Hanks balanced salt solution containing 20 mM Hepes, pH 7.5, and 1 mg/ml bovine serum albumin). The plates were then incubated with AP-OM-containing binding buffer for 75 min at room temperature. After extensive washing and heat inactivation, the bound proteins were detected by AP staining using nitro blue tetrazolium (NBT) and 5-bromo-4-chloro-3-indoyl phosphate (BCIP) as substrate. For saturation analysis, we disrupted cells and detected bound AP fusion proteins using r-nitrophenyl phosphate as substrate.

For expression cloning of OMgp-binding proteins, pools of 5,000 arrayed clones from a human brain cDNA library (Origene Technologies, Rockville, Md.) were transfected into COS-7 cells, and AP-OM binding was assessed as above. We isolated single NgR cDNA clones by sub-dividing the pools and sequencing analysis.

Generation of Recombinant Proteins and Viruses and Co-precipitation. To express recombinant OMgp for function assays, we subcloned the coding region of mouse OMgp (amino acids 23-392) into pSecTag B (Invitrogen) to express his-tagged OMgp protein (OM-his) in COS-7 cells. The expressed OM-his protein was purified using a nickel resin. To construct recombinant herpes simplex viruses (HSV), cDNAs for FLAG-tagged NgR or b-galatosidase were inserted into the HSV amplicon HSV-PrpUC and packaged into the virus using helper 5dl1.2, as described previously[20]. The resultant viruses were purified on sucrose gradients, pelleted, and resuspended in 10% sucrose. The titer of the viral stocks was 4.0×10[7] infectious units/ml. For each study, aliquots from the same batches of viral vectors were used. In order to produce recombinant Nogo-66 protein, the sequence of Nogo-66 was amplified from a human cDNA clone, KIAA0886, from the Kazusa DNA Research Institute and used to generate a construct expressing the AP-66 protein as described by GrandPre et al[6]. Antibodies against Nogo-A and MAG were purchased from Alpha Diagostics and R & D Systems, respectively.

In co-precipitation experiments, 2 mg GST or GST-NgR were first immobilized to glutathione-Agarose beads and the beads were further incubated with or without 1 mg OM-his in the presence of 2 mg of AP or AP-66 at 4° C. for 2 hr. After extensive washing, the bound proteins were resolved with SDS-PAGE and detected by Western blotting.

Growth Cone Collapse and Neurite Outgrowth Assays. Chick E13 DRG and E7 retina were isolated and cultured as described previously[9,10]. DRG explants cultured overnight were used for growth cone collapse assays. To assess the effects of PI-PLC treatment, cultures were pre-incubated with 2 U/ml PI-PLC for 30 min prior to treatment with individual test proteins for an additional 30 min. To express NgR in E7 retinal ganglion neurons, we infected the explants with recombinant HSV for 24 hr. After incubation with each test protein for 30 min, retinal explants were fixed in 4% paraformaldehyde and 15% sucrose. Infection of HSV-LacZ was detected by a standard b-galatosidase staining protocol[20]. FLAG-NgR expression was detected by incubating paraformaldehyde-fixed cultures with M2 anti-FLAG antibody (Sigma). Bound antibody was detected by incubation with AP-conjugated anti-rabbit IgG second antibody and reaction with NBT and BCIP (Vector labs). Growth cone collapse was quantified only in those positively stained for b-galatosidase or immunoreactive for the FLAG epitope.

Neurite outgrowth assays were performed as described previously[15,21]. Briefly, P7-9 rat CGNs were dissected and then plated at a density of 1×10[5] cells per well. The cells were cultured for 24 hr prior to fixation with 4% paraformaldehyde and staining with a neuronal specific anti-b-tubulin antibody (TuJ-1, Covance). Quantification of neurite length and statistical analysis were performed as described previously[22].

Oligodendrocyte precursor cells were isolated from the cerebral hemispheres of P1 rats and differentiated in vitro as described[3]. Immunostaining of mature oligodendrocytes was performed using antibodies against MBP (Sigma) and OMgp[14].

Exemplary OMgp Binding (OMgp-NgR Binding Inhibitory) Agents. An AP-OMgp fusion protein, prepared as described above, was used to evaluate the OMgp binding affinity of a variety of candidate binding agents as measured by the ability of agents preincubated with OMgp to inhibit subsequent OMgp-NgR binding. The selected binding assay formats are guided by structural requirements of the candidate agents and include COS-expression, solid phase ELISA-type assay, and fluorescent polarization assays. Candidate agents were selected from natural and synthetic peptide libraries biased to natural NgR LRR (supra) sequences, OMgp-specific monoclonal antibody (Mab) and Mab fragment libraries, a commercial fungal extract library, and a synthetic combinatorial organo-pharmacophore-biased library. In each instance, we assay specific binding inferentially by evaluating the affect of preincubating the OMgp with the agent, on subsequent OMgp-NgR binding. Selected exemplary high affinity OMgp-specific binding agents subject to in vivo activity assays (below) are shown in Table 2.

TABLE 2

Selected exemplary high-affinity OMgp-specific binding agents; (u), structure not yet determined.

| OMgp Binding Agent | Class/Source | Sequence/Structure | Binding Assay |
|---|---|---|---|
| 1. hNR260/308 | natural peptide | SEQ ID NO: 1 | ++++ |
| 2. mNR260/308 | natural peptide | SEQ ID NO: 2 | ++++ |
| 3. rNR260/308 | natural peptide | SEQ ID NO: 3 | ++++ |
| 4. s1NR260/308 | synthetic peptide | SEQ ID NO: 4 | ++++ |
| 5. s2NR260/308 | synthetic peptide | SEQ ID NO: 5 | ++++ |
| 6. s3NR260/308 | synthetic peptide | SEQ ID NO: 6 | ++++ |
| 7. OM-H2276 | monoclonal antibody | IgG | ++++ |
| 8. OM-H5831 | monoclonal antibody | IgG | ++++ |
| 9. OMF-H7712 | Fab fragment (Mab) | IgG Fab2 | ++++ |
| 10. OMF-H6290 | Fab fragment (Mab) | IgG Fab2 | ++++ |
| 11. XR-178892 | fungal extract library | natural (u) | ++++ |
| 12. XR-397344 | fungal extract library | natural (u) | ++++ |
| 13. XR-573632 | fungal extract library | natural (u) | ++++ |
| 14. SY-73273M | combinatorial library | synthetic (u) | ++++ |
| 15. SY-32340L | combinatorial library | synthetic (u) | ++++ |
| 16. SY-95734E | combinatorial library | synthetic (u) | ++++ |

Corticospinal Tract (CST) Regeneration Assay. High affinity OMgp binding agents demonstrating inhibition of OMgp-mediated in vitro axon growth cone collapse as described above are assayed for their ability to improve corticospinal tract (CST) regeneration following thoracic spinal cord injury by promoting CST regeneration into human Schwann cell grafts in the methods of Guest et al. (1997, supra). For these data, the human grafts are placed to span a midthoracic spinal cord transection in the adult nude rat, a xenograft tolerant strain. OMgp binding agents determined to be effective in in vitro collapse assays are incorporated into a fibrin glue and placed in the same region. Anterograde tracing from the motor cortex using the dextran amine tracers, Fluororuby (FR) and biotinylated dextran amine (BDA), are performed. Thirty-five days after grafting, the CST response is evaluated qualitatively by looking for regenerated CST fibers in or beyond grafts and quantitatively by constructing camera lucida composites to determine the sprouting index (SI), the position of the maximum termination density (MTD) rostral to the GFAP-defined host/graft interface, and the longitudinal spread (LS) of bulbous end terminals. The latter two measures provide information about axonal die-back. In control animals (graft only), the CST do not enter the graft and undergo axonal die-back. As shown in Table 3, the exemplified binding agents dramatically reduce axonal die-back and cause sprouting and these in vivo data are consistent with the corresponding growth cone collapsing activity.

TABLE 3

In Vitro and Vivo Neuronal Regeneration with Exemplery OMgp Binding Agents.

| OMgp Binding Agent | Collapse Inhibition | Reduced Die-Back | Promote Sprouting |
|---|---|---|---|
| 1. hNR260/308 | ++++ | ++++ | ++++ |
| 2. mNR260/308 | ++++ | ++++ | ++++ |
| 3. rNR260/308 | +++ | +++ | +++ |
| 4. s1NR260/308 | ++++ | ++++ | ++++ |
| 5. s2NR260/308 | +++ | +++ | +++ |
| 6. s3NR260/308 | ++++ | ++++ | ++++ |
| 7. OM-H2276 | ++++ | ++++ | ++++ |
| 8. OM-H5831 | ++++ | ++++ | ++++ |
| 9. OMF-H7712 | +++ | +++ | +++ |
| 10. OMF-H6290 | +++ | +++ | +++ |
| 11. XR-178892 | +++ | +++ | +++ |
| 12. XR-397344 | ++++ | ++++ | ++++ |
| 13. XR-573632 | ++++ | ++++ | ++++ |
| 14. SY-73273M | +++ | +++ | +++ |
| 15. SY-32340L | ++++ | ++++ | ++++ |
| 16. SY-95734E | +++ | +++ | +++ |

Peripheral Nerve Regeneration Assay. High affinity OMgp binding agents demonstrating inhibition of OMgp-mediated in vitro axon growth cone collapse as described above are also incorporated in the implantable devices described in U.S. Pat. No. 5,656,605 and tested for the promotion of in vivo regeneration of peripheral nerves. Prior to surgery, 18 mm surgical-grade silicon rubber tubes (I.D. 1.5 mm) are prepared with or without guiding filaments (four 10-0 monofilament nylon) and filled with test compositions comprising the binding agents of Table 2. Experimental groups consist of: 1. Guiding tubes plus Biomatrix 1T™ (Biomedical Technologies, Inc., Stoughton, Mass.); 2. Guiding tubes plus Biomatrix plus filaments; 3-23. Guiding tubes plus Biomatrix 1™ plus binding agents.

The sciatic nerves of rats are sharply transected at mid-thigh and guide tubes containing the test substances with and without guiding filaments sutured over distances of approximately 2 mm to the end of the nerves. In each experiment, the other end of the guide tube is left open. This model simulates a severe nerve injury in which no contact with the distal end of the nerve is present. After four weeks, the distance of regeneration of axons within the guide tube is tested in the surviving animals using a functional pinch test. In this test, the guide tube is pinched with fine forceps to mechanically stimulate sensory axons. Testing is initiated at the distal end of the guide tube and advanced proximally until muscular contractions are noted in the lightly anesthetized animal. The distance from the proximal nerve transection point is the parameter measured. For histological analysis, the guide tube containing the regenerated nerve is preserved with a fixative. Cross sections are prepared at a point approximately 7 mm from the transection site. The diameter of the regenerated nerve and the number of myelinated axons observable at this point are used as parameters for comparison.

Measurements of the distance of nerve regeneration document therapeutic efficacy. Similarly, plots of the diameter of the regenerated nerve measured at a distance of 7 mm into the guide tube as a function of the presence or absence of one or more binding agents demonstrate a similar therapeutic effect of all 16 tested. No detectable nerve growth is measured at the point sampled in the guide tube with the matrix-forming material alone. The presence of guiding filaments plus the matrix-forming material (no agents) induces only very minimal regeneration at the 7 mm measurement point, whereas dramatic results, as assessed by the diameter of the regenerating nerve, are produced by the device which consisted of the guide tube, guiding filaments and binding agent compositions. Finally, treatments using guide tubes comprising either a matrix-forming material alone, or a matrix-forming material in the presence of guiding filaments, result in no measured growth of myelinated axons. In contrast, treatments using a device comprising guide tubes, guiding filaments, and matrix containing binding agents compositions consistently result in axon regeneration, with the measured number of axons being increased markedly by the presence of guiding filaments.

OMgp-Specific Monoclonal Antibodies Promote Axon Regeneration In Vivo. In these experiments, our OM-H2276 and OM-H58310 Mgp-specific monoclonal antibodies are shown to promote axonal regeneration in the rat spinal cord. Tumors producing our OMgp-specific antibodies, implantation protocols and experimental design are substantially as used for IN-1 as described in Schnell et al., Nature 1990 Jan. 18; 343(6255):269-72. In brief, our OM-H2276 and OM-H5831 monoclonal antibodies are applied intracerebrally to young rats by implanting antibody-producing tumours. In 2-6-week-old rats we make complete transections of the corticospinal tract, a major fibre tract of the spinal cord, the axons of which originate in the motor and sensory neocortex. Previous studies have shown a complete absence of corticospinal tract regeneration after the first postnatal week in rats, and in adult hamsters and cats. In our treated rats, significant sprouting occurs at the lesion site, and fine axons and fascicles can be observed up to 7-11 mm caudal to the lesion within 2-3 weeks. In control rats, a similar sprouting reaction occurs, but the maximal distance of elongation rarely exceeded 1 mm. These results demonstrate the capacity for CNS axons to regenerate and elongate within differentiated CNS tissue after neutralization of OMgp-mediated axon growth inhibition.

OMgp-Specific Monoclonal Antibody Fragments Promote Axon Regeneration in Vivo. In these experiments, OMgp-specific monoclonal antibody fragments are shown to promote sprouting of Purkinje cell axons. Experimental protocols were adapted from Buffo et al., 2000, J Neuroscience 20, 2275-2286.

Animals and surgical procedures. Adult Wistar rats (Charles River, Calco, Italy) are deeply anesthetized by means of intraperitoneal administration of a mixture of ketamine (100 mg/kg, Ketalar; Bayer, Leverkusen, Germany) and xylazine (5 mg/kg, Rompun; Bayer).

Fab fragment or antibody injections are performed as previously described (Zagrebelsky et al., 1998). Animals are placed in a stereotaxic apparatus, and the dorsal cerebellar vermis exposed by drilling a small hole on the posterosuperior aspect of the occipital bone. The meninges are left intact except for the small hole produced by the injection pipette penetration. In test rats a recombinant Fab fragment of the OM-H2276 and OM-H5831 antibodies (produced in *E. coli*), which neutralizes OMgp-associated axon growth cone collapse in vitro is injected into the cerebellar parenchyma. Three 1 μl injections of Fab fragments in saline solution (5 mg/ml) are performed 0.5-1 mm deep along the cerebellar midline into the dorsal vermis (lobules V-VII). The injections are made by means of a glass micropipette connected to a PV800 Pneumatic Picopump (WPI, New Haven, Conn.). The frequency and duration of pressure pulses are adjusted to inject 1 μl of the solution during a period of ~10 min. The pipette is left in situ for 5 additional minutes to avoid an excessive leakage of the injected solution. As a control, an affinity-purified F(ab')$_2$ fragment of a mouse anti-human IgG (Jackson ImmunoResearch Laboratories, West Grove, Pa.) is applied to another set of control rats using the same procedure. Survival times for these two experimental sets are 2, 5, 7 and 30 d (four animals for each time point). An additional set of intact animals are examined as untreated controls.

Histological procedures. At different survival times after surgery, under deep general anesthesia (as above), the rats are transcardially perfused with 1 ml of 4% paraformaldehyde in 0.12 M phosphate buffer, pH 7.2-7.4. The brains are immediately dissected, stored overnight in the same fixative at 4° C., and finally transferred in 30% sucrose in 0.12 M phosphate buffer at 4° C. until they sink. The cerebella are cut using a freezing microtome in several series of 30-μm-thick sagittal sections. One series is processed for NADPH diaphorase histochemistry. These sections are incubated for 3-4 hr in darkness at 37° C. in a solution composed of -NADPH (1 mg/ml, Sigma, St. Louis, Mo.) and nitroblue tetrazolium (0.2 mg/ml, Sigma) in 0.12 M phosphate buffer with 0.25% Triton X-100. In some cases (two animals per treated and control sets at 2 and 5 d survival), microglia are stained by incubating one section series with biotinylated *Griffonia simplicifolia* isolectin B4 [1:100 in phosphate buffer with 0.25% Triton X-100; Sigma (Rossi et al., 1994a)] overnight at 4° C. Sections are subsequently incubated for 30 min in the avidin-biotin-peroxidase complex (Vectastain, ABC Elite kit, Vector, Burlingame, Calif.) and revealed using the 3,3' diaminobenzidine (0.03% in Tris HCl) as a chromogen.

All of the other series are first incubated in 0.3% $H_2O_2$ in PBS to quench endogenous peroxidase. Then, they are incubated for 30 min at room temperature and overnight at 4° C. with different primary antibodies: anti-calbindin D-28K (monoclonal, 1:5000, Swant, Bellinzona, Switzerland), to visualize Purkinje cells; anti-c-Jun (polyclonal, 1:1000, Santa Cruz Biotechnology, Santa Cruz, Calif.); and anti-CD11b/c (monoclonal OX-42, 1:2000, Cedarlane Laboratories, Homby, Ontario) to stain microglia. All of the antibodies are diluted in PBS with 0.25% Triton X-100 added with either normal horse serum or normal goat serum depending on the species of the second antibody. Immunohistochemical staining is performed according to the avidin-biotin-peroxidase method (Vectastain, ABC Elite kit, Vector) and revealed using the 3,3' diaminobenzidine (0.03% in Tris HCl) as a chromogen. The reacted sections are mounted on chrome-alum gelatinized slides, air-dried, dehydrated, and coverslipped.

Quantitative analysis. Quantification of reactive Purkinje cells in the different experiments is made by estimating the neurons labeled by c-Jun antibodies as previously described (Zagrebelsky et al., 1998). For each animal, three immunolabeled sections are chosen. Only vermal sections close to the cerebellar midline that contain the injection sites are considered. The outline of the selected sections is reproduced using the Neurolucida software (MicroBrightField, Colchester, Vt.) connected to an E-800 Nikon microscope, and the position of every single-labeled cell carefully marked. The number of labeled cells present in the three reproduced sections is averaged to calculate values for every individual animal, which are used for statistical analysis carried out by Student's test.

A morphometric analysis of Purkinje axons in the different experimental conditions for each animal, is performed using three anti-calbindin-immunolabeled sections, contiguous to those examined for c-Jun, as described in Buffo et al. (supra). Morphometric measurements are made on 200×250 μm areas of the granular layer chosen by superimposing a grid of this size on the section. The selected areas encompass most of the granular layer depth and contain only minimal portions of Purkinje cell layer or axial white matter. In each of the selected sections is sampled one area from the dorsal cortical lobules and one from the ventral cortical lobules. In addition, to sample from the different parts of these two cortical regions, areas from different lobules are selected in the three sections belonging to each individual animal, one area in each of lobules V, VI, and VII and one in lobules I, II, and IX. All of the anti-calbindin-immunolabeled Purkinje axon segments contained within the selected areas are reproduced using the Neurolucida software (MicroBrightField) connected to an E-800 Nikon microscope with 20× objective, corresponding to 750× magnification on the computer screen. Each labeled axon segment or branch is reproduced as a single profile. From these reproductions the software calculates the number of axon profiles, their individual length, and the total length of all the reproduced segments, the mean profile length (total length/number of profiles), and the number of times that the axons crossed a 25×25 μm grid superimposed on the selected area. Data calculated from the different areas in the three sections sampled from each cerebellum are averaged to obtain values for every individual animal. Statistical analysis is performed on the latter values (n=4 for all groups at all time points) by Student's t test and paired t test.

Our results reveal significant promotion of sprouting of Purkinje cell axons in test rats subject to our OM-H2276 and OM-H58310 Mgp-specific monoclonal antibody fragments as compared with the control animals.

FOOTNOTED REFERENCES

1. Schwab, M. E., and Bartholdi, D. Degeneration and regeneration of axons in the lesioned spinal cord. *Physiol. Rev.* 76, 319-370 (1996).
2. Horner, P. J. Gage, F. H. Regenerating the damaged central nervous system. *Nature* 407, 963-970 (2000).
3. McKerracher, L et al., Identification of myelin-associated glycoprotein as a major myelin-derived inhibitor of neurite growth. *Neuron* 13, 805-811 (1994).
4. Mukhopadhyay, G. et al., A novel role for myelin-associated glycoprotein as an inhibitor of axonal regeneration. *Neuron* 13, 757-767 (1994).
5. Chen, M. S. et al., Nogo-A is a myelin-associated neurite outgrowth inhibitor and an antigen for monoclonal antibody IN-1. *Nature* 403, 434-439 (2000).
6. GrandPre, T., Nakamura, F., Vartanian, T., Strittmatter, S. M. Identification of the Nogo inhibitor of axon regeneration as a Reticulon protein. *Nature* 403, 439-444 (2000).
7. Prinjha, R. et al., Inhibitor of neurite outgrowth in humans. *Nature* 403, 383-384 (2000).
8. Tessier-Lavigne, M, Goodman, C. S. Perspectives: neurobiology. Regeneration in the Nogo zone. *Science* 287, 813-814 (2000).
9. Fournier, A. E., GrandPre, T., Strittmatter, S. M. Identification of a receptor mediating Nogo-66 inhibition of axonal regeneration. *Nature* 409, 341-346 (2001); see also, Strittmatter, US2002/0012965.
10. Luo, Y., Raible, D., Raper, J. A. Collapsin: a protein in brain that induces the collapse and paralysis of neuronal growth cones. *Cell* 75, 217-227 (1993).
11. Mikol, D. D., Stefansson, K. A phosphatidylinositol-linked peanut agglutinin-binding glycoprotein in central nervous system myelin and on oligodendrocytes. *J Cell Biol* 106, 1273-1279 (1988).
12. Mikol, D. D., Gulcher, J. R., Stefansson, K. The oligodendrocyte-myelin glycoprotein belongs to a distinct family of proteins and contains the HNK-1 carbohydrate. *J Cell Biol* 110, 471-479 (1990).
13. He, Z, and Tessier-Lavigne, M. Neuropilin is a receptor for the axonal chemorepellent Semaphorin III. *Cell* 90, 739-751, 1997.
14. Habib, A. A., Marton L. S., Allwardt, B., Gulcher, J. R., Mikol, D. D., Hognason, T., Chattopadhyay, N., Stefansson, K. Expression of the oligodendrocyte-myelin glycoprotein by neurons in the mouse central nervous system. *J Neurochem* 70, 1704-1711 (1998).
15. Niederost, B. P., Zimmermann, D. R., Schwab, M. E., Bandtlow, C. E. Bovine CNS myelin contains neurite growth-inhibitory activity associated with chondroitin sulfate proteoglycans. *J Neurosci* 19, 8979-8989 (1999).
16. Spillmann, A. A., Bandtlow, C. E., Lottspeich, F., Keller, F., Schwab, M. E Identification and characterization of a bovine neurite growth inhibitor (bNI-220). *J Biol Chem* 273, 19283-19293 (1998).
17. Flanagan, J. G. and Cheng, H.J. Alkaline phosphatase fusion proteins for molecular characterization and cloning of receptors and their ligands. *Methods Enzymol* 327, 198-210 (2000).
18. Liu B. P, Strittmatter S. M. Semaphorin-mediated axonal guidance via Rho-related G proteins. *Curr Opin Cell Biol* 13, 619-626 (2001).
19. Norton, W. T., and Poduslo, S. E. Myelination in rat brain: method of myelin isolation. *J. Neurochem.* 21, 749-757 (1973).
20. Neve, R. L, Howe, J. R, Hong, S, Kalb, R. G. Introduction of the glutamate receptor subunit 1 into motor neurons in vitro and in vivo using recombinant herpes simplex virus. *Neuroscience* 79, 435-447 (1997).
21. Huang, D. W., McKerracher, L., Braun, P. E., David, S. A therapeutic vaccine approach to stimulate axon regeneration in the adult mammalian spinal cord. *Neuron* 24, 639-647 (1999).
22. Cohen-Cory, S, and Fraser, S. E. Effects of brain-derived neurotrophic factor on optic axon branching and remodeling in vivo. *Nature* 378, 192-196 (1995).
23. Oka, A., Belliveau, M. J., Rosenberg, P. A., and Volpe, J. J. Vulnerability of oligodendroglia to glutamate: Pharmacology, mechanisms and prevention. *J. Neurosci.* 13, 1441-1453 (1993).
24. Takahashi, T., Nakamura, F., Jin, Z., Kalb, R. G., Strittmatter, S. M. Semaphorins A and E act as antagonists of neuropilin-1 and agonists of neuropilin-2 receptors. *Nat Neurosci* 1, 487-493 (1998).

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for characterizing an agent as inhibiting binding of NgR (Nogo receptor) to OMgp (oligodendrocyte-myelin glycoprotein), the method comprising the steps of:

incubating a mixture comprising NgR, OMgp and an agent under conditions whereby but for the presence of the agent, the NgR and OMgp exhibit a control binding; and specifically detecting a reduced binding of the NgR to the OMgp, indicating that the agent inhibits binding of the NgR to the OMgp.

2. A method according to claim 1, wherein at least one of the NgR and OMgp is soluble.

3. A method according to claim 1, wherein one of the NgR and OMgp is soluble and the other is membrane-bound.

4. A method according to claim 1, wherein at least one of the NgR and OMgp is recombinantly expressed on a surface of a cell.

5. A method according to claim 1 wherein the agent is preincubated with the OMgp to inhibit subsequent OMgp-NgR binding.

6. A method according to claim 1 wherein the method comprises a format selected from the group consisting of COS-expression, solid phase ELISA-type assay, and fluorescent polarization assay.

7. A method according to claim 1 wherein the agent is selected from natural and synthetic peptide libraries biased to natural NgR LRR sequences, OMgp-specific monoclonal antibody (Mab) and Mab fragment libraries, a commercial fungal extract library, and a synthetic combinatorial organo-pharmacophore-biased library.

8. A method according to claim 1 wherein the method comprises a corticospinal tract (CST) regeneration assay format.

9. A method according to claim 1 wherein the method comprises a peripheral nerve regeneration assay format.

* * * * *

SEQUENCE LISTING

<160> NUMBER OF SEQ ID NOS: 6

<210> SEQ ID NO 1

```
<211> LENGTH: 49
<212> TYPE: PRT
<213> ORGANISM: human

<400> SEQUENCE: 1

Asn Pro Trp Val Cys Asp Cys Arg Ala Arg Pro Leu Trp Ala Trp Leu
 1               5                  10                  15

Gln Lys Phe Arg Gly Ser Ser Ser Glu Val Pro Cys Ser Leu Pro Gln
            20                  25                  30

Arg Leu Ala Gly Arg Asp Leu Lys Arg Leu Ala Ala Asn Asp Leu Gln
        35                  40                  45

Gly

<210> SEQ ID NO 2
<211> LENGTH: 49
<212> TYPE: PRT
<213> ORGANISM: mouse

<400> SEQUENCE: 2

Asn Pro Trp Val Cys Asp Cys Arg Ala Arg Pro Leu Trp Ala Trp Leu
 1               5                  10                  15

Gln Lys Phe Arg Gly Ser Ser Ser Glu Val Pro Cys Asn Leu Pro Gln
            20                  25                  30

Arg Leu Ala Asp Arg Asp Leu Lys Arg Leu Ala Ala Ser Asp Leu Glu
        35                  40                  45

Gly

<210> SEQ ID NO 3
<211> LENGTH: 49
<212> TYPE: PRT
<213> ORGANISM: bovine

<400> SEQUENCE: 3

Asn Pro Trp Val Cys Asp Cys Arg Ala Arg Pro Leu Trp Ala Trp Leu
 1               5                  10                  15

Gln Lys Phe Arg Gly Ser Ser Ser Gly Val Pro Ser Asn Leu Pro Gln
            20                  25                  30

Arg Leu Ala Gly Arg Asp Leu Lys Arg Leu Ala Thr Ser Asp Leu Glu
        35                  40                  45

Gly

<210> SEQ ID NO 4
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 4

Pro Ala Leu Cys Leu Cys Arg Ala Arg Pro Leu Trp Ala Trp Leu Gln
 1               5                  10                  15

Lys Phe Arg Gly Ser Ser Ser Glu Val Pro Cys Ser Leu Pro Gln Arg
            20                  25                  30

Leu Ala Gly Arg Asp Leu Lys Arg Leu Ala Ala Asn Asp Leu Ala
        35                  40                  45

<210> SEQ ID NO 5
<211> LENGTH: 40
<212> TYPE: PRT
```

-continued

```
<213> ORGANISM: Artificial Sequence
<220> FEATURE:
<223> OTHER INFORMATION: Description of Artificial Sequence: Synthetic
      peptide sequence

<400> SEQUENCE: 5

Arg Pro Leu Trp Ala Trp Leu Gln Lys Phe Arg Gly Ser Ala Ser Glu
  1               5                  10                  15

Val Pro Cys Ser Leu Pro Gln Arg Leu Ala Gly Arg Asp Leu Lys Arg
                 20                  25                  30

Leu Ala Ala Asn Asp Leu Gln Gly
             35                  40

<210> SEQ ID NO 6
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 6

Gln Pro Ala Val Leu Asp Cys Arg Ala Arg Pro Leu Trp Ala Trp Leu
  1               5                  10                  15

Gln Lys Phe Arg Gly Ser Ser Ser Glu Val Pro Leu Ser Leu Pro Gln
                 20                  25                  30

Arg Leu Ala Gly Arg Asp Leu Lys Arg Leu Ala
             35                  40
```